United States Patent [19]

Felthouse

[11] Patent Number: 4,582,650
[45] Date of Patent: Apr. 15, 1986

[54] OXIDATION WITH ENCAPSULATED CO-CATALYST

[75] Inventor: Timothy R. Felthouse, St. Louis, Mo.

[73] Assignee: Monsanto Company, St. Louis, Mo.

[21] Appl. No.: 700,170

[22] Filed: Feb. 11, 1985

[51] Int. Cl.$^4$ ............................................. C07F 9/38
[52] U.S. Cl. .......................... 260/502.5 F; 423/437; 502/74
[58] Field of Search ............... 260/502.5 F; 423/437, 423/580

[56] References Cited

U.S. PATENT DOCUMENTS

| | | | |
|---|---|---|---|
| 3,373,109 | 3/1968 | Frilette et al. | 252/455 |
| 3,907,652 | 9/1975 | Wagenknecht et al. | 260/502.5 F |
| 3,950,402 | 4/1976 | Franz | 260/502.5 F |
| 3,954,848 | 5/1976 | Franz | 260/502.5 F |
| 3,969,398 | 7/1976 | Hershman | 260/502.5 F |
| 4,147,719 | 4/1979 | Franz | 260/502.5 F |
| 4,299,686 | 11/1981 | Kuehl | 208/111 |
| 4,380,663 | 4/1983 | Roscher et al. | 423/437 |
| 4,486,356 | 12/1984 | Bakel | 260/502.5 F |
| 4,507,250 | 3/1985 | Bakel | 260/502.5 F |

FOREIGN PATENT DOCUMENTS 2049697 12/1980 United Kingdom ......... 260/502.5 F

OTHER PUBLICATIONS

Shape-Selective Platinum/ZSM-5 Catalysts, R. M. Dessau, *Journal of Catalysis* 89, 520–526 (1984).
Huang, T. N., Schwartz, *J. Am. Chem. Soc.* 1982, 104, 5244–5245.

*Primary Examiner*—J. E. Evans
*Attorney, Agent, or Firm*—Joseph D. Kennedy; James W. Williams, Jr.

[57] ABSTRACT

Processes are given for which a microcrystalline support having a noble metal located within its pores, is used as a permselective catalyst to oxidize formaldehyde and similar materials while avoiding poisoning by N-phosphonomethylamines. The permselective catalyst can be used as a co-catalyst with activated carbons in the oxidation of N-phosphonomethyliminodiacetic acid to N-phosphonomethylglycine.

11 Claims, No Drawings ns for penetration. The size of the openings
OXIDATION WITH ENCAPSULATED CO-CATALYST The present invention relates to methods for catalyzed oxidation of formaldehyde in the presence of N-phosphonomethylamines, as in methods of preparing N-phosphonomethylglycine by oxidative cleavage of N-phosphonomethyliminodiacetic acid with concurrent oxidation of the formaldehyde side product produced in the reaction, and to catalysts useful in such reactions. In particular, the invention concerns the use of noble metal-microcrystalline support catalysts, in which the noble metal is located within the pores of the support, along with carbon catalysts in such reactions; and the preparation of such catalysts in which the noble metal is relatively inaccessible to poisoning by N-phosphonomethylamines.

BACKGROUND OF THE INVENTION

One of the most prominent of present day herbicides is N-phosphonomethylglycine or its derivatives. The N-phosphonomethylglycine compound can be prepared by the oxidation of N-phosphonomethyliminodiacetic acid, employing activated carbon as the catalyst, as described in U.S. Pat. No. 3,969,398. In such oxidation, one of the by-products is formaldehyde, and formaldehyde has some tendency to react with and methylate amino compounds, including the desired N-phosphonomethylglycine. Zeolites and synthetic zeolites are known materials which have been employed in various ways as catalysts and catalyst support materials. U.S. Pat. No. 4,299,686 asserts methods of preparing zeolite Alpha containing platinum group metal within the pores and its use in processes requiring shape selectivity for straight-chain compounds for selectoforming, hydrodewaxing, selective cracking, etc. U.S. Pat. No. 3,373,109 refers to having a minor part of metal dispersed within the pores of a crystalline aluminosilicate, and for example, describe materials having channels which permit adsorption and pore diffusion of normal paraffins and olefins having a molecular size smaller than 5 angstroms, and refer to selective high activity restricted to those molecules which do not exceed a maximum critical diameter.

SUMMARY OF THE INVENTION

The invention involves a process for catalyzed oxidation of formaldehyde or formic acid in the presence of N-phosphonomethylglycine, utilizing a noble metal catalyst which is located within the pores of zeolite or other microcrystalline support, in order to avoid or impede contact by the N-phosphonomethylglycine or other process impurities while permitting contact by the formaldehyde. The invention is particularly concerned with effecting such oxidation of formaldehyde during the production of N-phosphonomethylglycine by carbon-catalyzed oxidative cleavage of N-phosphonomethyliminodiacetic acid, as formaldehyde is a by-product in the cleavage reaction and may further react with the desired N-phosphonomethylglycine product.

The invention is further concerned with use of the referred-to noble catalyst in a microporous support, possibly in the presence of activated carbon catalyst, to treat effluent from reactions to produce N-phosphonomethylglycine, to remove formaldehyde therefrom; such effluent may contain amounts of N-phosphonomethylglycine, N-phosphonomethyliminodiacetic acid, or other phosphonomethylamines or amino compounds, or reaction impurities. The invention is further concerned with combination catalysts, comprising an activated carbon catalyst and a catalyst comprised of a noble metal dispersed within the pore structure of a microporous support.

DETAILED DESCRIPTION

The present invention involves the use of noble metal catalysts in which the metal is protected from poisoning by being embedded within the pores of a microporous support. The nature of the support and the location of the metal therein is such as to make the metal relatively inaccessible to poisons, thereby extending the life of the catalyst. Ideally, the support will have pores such that the poison is too bulky to penetrate to the metal in the pores, while formaldehyde or other species to be reacted can readily reach the metal. Aside from selectivity based strictly upon size, surface effects can be involved, and particular surface groups can inhibit entry by a compound, even though the compound may appear to be of sufficiently small size to penetrate the pores. The noble metal catalyst materials for use herein have the noble metal located within the pores of a microporous support material, as determined by transmission electron microscopy. Such catalyst materials are referred to herein as encapsulated, although recognizing that the microporous nature of the support provides some openings for penetration. The size of the openings has a significant relationship to penetrability of the support, but large-pore zeolites can be used herein, referring to those with 12 or so ring members. Many of the useful zeolites have 8–10 or fewer ring members, and may, for example, have pore openings of 5 Å. In general, a small molecule such as formaldehyde readily penetrates zeolites, so most of the available zeolite pore sizes are suitable, so far as formaldehyde permeation is concerned. However, difficulties may be encountered in incorporating a noble meal into the channels of some of the very small-pore zeolites. The noble metals will typically be in the form of very small crystallites or particles in order to fit within the voids of the support, such as in the range of about 10 to 20 Å, but larger or smaller particles can be present. However, a substantial amount of the metal crystallites should have diameters no greater than 20 Å, in order to be relatively inaccessible to contact by large molecules. If crystallites of such size are present, they will typically be located within the pores and provide permselective catalytic properties, even though metal crystallites of substantially larger size are also present. The larger size crystallites will be subject to poisoning by such compounds as N-phosphonomethylamines, making the metal in such form relatively ineffective for desired uses, but the accompanying embedded crystallites of less than 20 Å diameter can still have the desired effect.

The present noble metal catalyst materials are designed for semipermeability, i.e., to permit permeation or penetration by species to be oxidized, while hindering penetration by catalyst poisons, such as N-phosphonomethylglycine. With some types of support materials, it may be feasible to have almost complete exclusion of permeation to the metal by the N-phosphonomethylglycine. With other support materials where there is some penetration by the poison, there can still be advantage if the rate of penetration of the formaldehyde or formic acid reactant is many times greater than that of the N-phosphonomethylglycine poison. Since, formaldehyde and formic acid readily penetrate the zeolite materials, a marked hindrance of N-phosphonomethylglycine passage can cause a large difference in rates. In addition to effects of pore size in excluding the larger molecules, diffusion factors may have a significant effect on the penetration rate, particularly in the liquid reaction systems contemplated in the present invention. While penetration rates have not been measured, the rates of formaldehyde may well be several hundred times or more greater than that of N-phosphonomethylglycine. In terms of advantage, it is desirable that the encapsulated noble metal catalyst have two or more times the life of the unencapsulated catalyst, and in fact it may ultimately be feasible for practical operation to have catalyst life many times that of the unencapsulated catalyst and sufficient to make replacement or regeneration of the noble metal catalyst a minor factor in process economics. Moreover, with regard to regeneration, it has been found that the encapsulated catalysts herein are amenable to ready regeneration by simple procedures.

The present invention is particularly concerned with a reaction to prepare N-phosphonomethylglycine by oxidative cleavage of N-phosphonomethyliminodiacetic acid,

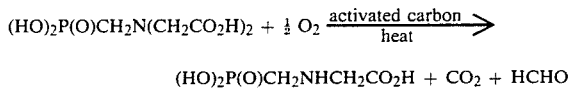

The reaction works well, and is a suitable process for preparing N-phosphonomethylglycine. However, the formaldehyde by-product has a tendency to react further with amines, including the desired N-phosphonomethylglycine and other N-phosphonomethylamines, thereby detracting from yield of the desired product. The present invention overcomes this problem by using a co-catalyst along with the carbon, so that the formaldehyde is further oxidized to carbon dioxide and water, thereby becoming unavailable for reaction with the N-phosphonomethylglycine product, as illustrated by the following equation:

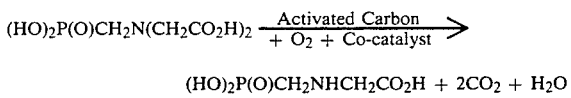

In carrying out the reaction, it is important to protect the co-catalyst from ready contact by the N-phosphonomethylamines present, as noble metal crystallite catalysts are quickly poisoned by such compounds. In the illustrated reaction showing formaldehyde as a by-product, some of the formaldehyde may be converted to formic acid which can similarly undergo interfering reactions, and in the present invention the formic acid can also be oxidized to carbon dioxide and water.

The present invention can use various noble metals for the co-catalysts, e.g., Ru, Os, Rh, Ir, Pd and Pt, with Rh or Pt generally being preferred. The amount of noble metal in the microporous support can vary widely, but will generally be in the range of above 0.1% to about 5% by weight, and amounts of about 3% or so are suitable for illustration.

In accordance with an embodiment of this invention, N-phosphonomethyliminodiacetic acid is dissolved in water and this solution contacted with a molecular oxygen-containing gas in the presence of activated carbon and a zeolite encapsulated co-catalyst, while heating the mixture to a temperature sufficiently elevated to cause said oxygen and said N-phosphonomethyliminodiacetic acid to react to produce N-phosphonomethyl glycine.

The temperature employed in carrying out the oxidation process should be sufficient to initiate the reaction and to sustain the reaction once initiated. Temperatures of from about 25° C., to 150° C. or even higher are usually satisfactory. As those skilled in the art would realize, at lower temperatures the rate of reaction is undesirably slow and, therefore, temperatures of at least 75° C. are preferred and even more preferred are temperatures in the range of about 90° C. to 150° C. It is, of course, realized that at temperatures above about 100° C. that pressure will have to be maintained on the system to maintain a liquid phase.

The pressure at which the process to prepare N-phosphonomethylglycine is conducted can vary over wide ranges. Thus, the pressure of the molecular oxygen-containing gas can be as low as 50 kPa to 20,000 kPa or higher. It is preferred for convenience to conduct the process at a total pressure of from about 50 kPa to 20,000 kPa. It is even more preferred to conduct the process at pressures of from ambient atmospheric pressure to 700 kPa.

The manner in which the aqueous solution of the N-phosphonomethyliminodiacetic acid is contacted with the molecular oxygen-containing gas and activated carbon and co-catalyst can vary greatly. For example, the N-phosphonomethyliminodiacetic acid solution can be placed in a closed container with some free space containing molecular oxygen and shaken vigorously or agitated by stirring or the molecular oxygen-containing gas can be bubbled through said solution containing activated carbon and co-catalyst either through a straight tube or a tube with a fritted diffuser attached thereto. The contacting can also be accomplished in a tubular continuous reactor packed with activated carbon and co-catalyst. Thus, the process of this invention only requires actively contacting the molecular oxygen containing gas with the aqueous solution of said N-phosphonomethylimino diacetic acid containing said activated carbon catalyst and co-catalyst.

In conducting the oxidation process it is often preferred to employ approximately saturated solutions of the N-phosphonomethyliminodiacetic acid in water at the temperature of reaction for ease of reaction and ease of recovery of the product, N-phosphonomethylglycine, i.e., from about 1% by weight at 25° C., about 4% by weight at 95° C. It is, of course, possible to employ very dilute, i.e., 0.1% by weight of N-phosphonomethyliminodiacetic acid in water; however, this results in a more difficult product recovery procedure.

The reaction, of course, occurs in the aqueous phase when the solution comes in contact with the presence of the catalyst. Thus it is possible to use supersaturated solutions or slurries in which the reactant removed from solution by the oxidation reaction is replaced by the dissolution of more reactant. This maintains the amount of available reactant at a maximum and is therefore preferred to operating in a highly dilute solution.

The amount of the molecular oxygen-containing gas employed can vary over wide ranges. It is, of course, obvious to those skilled in the art that the best yields of the N-phosphonomethylglycine are produced when at least stoichiometric amounts of oxygen are employed.

In most instances for ease of reaction and best yields of the final product, N-phosphonomethylglycine, the amount of oxygen employed would ordinarily be at least ½ mole of oxygen for each mole of N-phosphonomethyliminodiacetic acid employed. In actual practice, the amount of oxygen employed will be from ½ to 1 or more moles for each mole of the N-phosphonomethyliminodiacetic acid employed since the efficiency of the oxygen utilization is usually less than 100%.

By the term "molecular oxygen-containing gas", as employed herein, is meant any gaseous mixture containing molecular oxygen with one or more diluents which are non-reactive with the oxygen or with the reactant or product under the conditions of reaction. Examples of such gases are air, oxygen, oxygen diluted with helium, argon, nitrogen, or other inert gas, oxygen-hydrocarbon mixtures and the like. It is preferred to employ gases containing 20 or more percent by weight molecular oxygen and even more preferred to employ gases containing 90 or more percent by weight molecular oxygen.

The activated carbon catalysts employed in the process of this invention are well known in the art and are available under a large number of trade names. These activated carbons are characterized by high adsorptive capacity for gases, vapors, various molecules dissolved in solution, and colloidal solids and relatively high specific surface areas. Carbon, char or charcoal is produced by destructive distillation of wood, peat, lignite, nut shells, bones, vegetable or other natural or synthetic carbonaceous matter, but must usually be "activated" to develop adsorptive power. Activation is usually achieved by heating to high temperatures (800°-900° C.) with steam or with carbon dioxide, which brings about a porous particle structure and increased specific surface area. In some cases hygroscopic acid or sodium sulfate, are added prior to the destructive distillation or activation, to increase adsorptive capacity. The carbon content of active carbons ranges from about 10% for bone charcoal to about 98% for some wood chars and nearly 100% for activated carbons derived from organic polymers. The non-carbonaceous matter in activated charcoal will vary depending on precursor origin and/or activation procedure. For example, inorganic "ash" components containing aluminum and silicon are oftentimes present in large amounts accompanied by certain alkali metals and alkaline earths. The later grouping influences the acidity-basicity characteristics of the activated carbon. Other inorganic constituents found in many activated carbons include iron and titanium. Depending on raw material original and activation procedure, large amounts of oxygen can be present along with lesser amounts of hydrogen, nitrogen and sulfur. Oxygen content also influences activated carbon acidity-basicity.

The specific surface area of activated carbons used herein, measured by the BET (Brunauer-Emmett-Teller) method using $N_2$ can range from 100 to nearly 2000 m²/g. The packed bulk density of activated carbons will depend on the form (powder vs. particulate) and also on the measuring technique employed. Measured values less than 0.15 g/cc and as high or about 0.6 g/cc for powders have been recorded.

The amount of granular or powdered activated carbon employed in the oxidation process can range from 0.5 to 100 or more parts by weight for every 100 parts by weight of the N-phosphonomethyliminodiacetic acid employed. For the powdered activated carbons, it is preferred to employ from 1 to 50 parts by weight of activated carbon for 100 parts by weight of the N-phosphonomethyliminodiacetic acid. For the activated carbons in granular forms, it is preferred to employ 1 to 75 parts by weight per 100 parts by weight of N-phosphonomethyliminodiacetic acid and a more prescribed range is from 20 to 60 parts by weight. It is, of course, obvious that in a tubular type reactor, hereinbefore mentioned, weight ratios of activated carbon to reactants can vary over even greater ranges than herein set forth. The amount of zeolite encapsulated catalyst can be varied as found most effective, but will generally be in the range of 2 to 15 or 20 parts by weight (metal+-zeolite) per 100 parts by weight carbon catalyst, and about 5 parts is a convenient amount. The activated carbon employed can be in the form of powders or granules, and the zeolite encapsulated catalyst can be in similar form. Further description of procedures for oxidizing N-phosphonomethyliminodiacetic acid are found in Hershman U.S. Pat. No. 3,969,398, the disclosure of which is incorporated herein by reference. The activated carbons disclosed by way of example in that patent can suitably be used for the present oxidations. The encapsulated zeolite catalyst can be mixed with the carbon catalyst prior to use as a co-catalyst in a process, or it can be added to a reaction medium to which a carbon catalyst is also added, and used as a co-catalyst therein. Of course, when both catalysts are in a reaction medium, they will become admixed therein, and generally will still be mixed together when recovered from the process, or used in recycle procedures.

The amount of zeolite encapsulated catalyst can also be considered with respect to the formaldehyde or other materials to be oxidized, and the medium containing materials to be oxidized, especially in the event waste streams are being treated subsequent to a reaction. While the catalyst can be used over broad ranges of concentrations, relatively low concentrations are often effective, such as in the range of about 0.01% to 0.5% or slightly higher, of the reaction medium, with the percentages being calculated on the total weight of platinum or other noble metal and zeolite present. The percentages, of course, would be much smaller if based on the small amount of catalytic metal present and encapsulated in the zeolite.

In illustrated reactions herein, the phosphonomethyl group has been shown with a free phosphonic acid, i.e., with two −OH groups on the phosphorus. However, the present catalyst system can be usefully employed in the presence of N-phosphonomethylamines in general, including those in which the phosphono moiety is in ester or in salt form; and similarly the diacetic acid groups in the iminodiacetic acid can be in ester or salt form, with operating reactants being illustrated

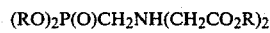

$(RO)_2P(O)CH_2NH(CH_2CO_2R)_2$ in which each R is individually selected from hydrogen, or salt or ester forming groups, Exemplifications of suitable ester forming groups are hydrocarbyl groups, particularly short-chain alkyl groups such as methyl and ethyl groups. Alkali metal, e.g., sodium or potassium, alkaline earth metal and ammonium salts can conveniently be used. The oxidation reaction is conveniently conducted in water, but other solvents can be employed, e.g., glacial acetic acid, aqueous acetic acid, or various other solvents which are resistant to oxidation under the reaction conditions. Illustrative of other solvents or liquids which can be used are nitriles such as acetonitrile, propionitrile, etc.; nitrocompounds such as nitromethane, and halogenated compounds such as methylene chloride.

The microcrystalline supports used herein are three-dimensional aluminosilicates, zeolites, and it is advisable to select such materials so as to have sufficient acid stability as not to undergo excessive degradation (compositional and/or crystallinity changes) under the conditions of employment, such as in the presence of $(HO)_2P(O)CH_2NR^1R^2$, where $R^1$ and $R^2$ are organic groups or hydrogen, in aqueous solution at elevated temperatures. Aluminosilicates with an Si/Al ratio of about 2 or more will generally have sufficient acid stability. Examples of zeolites which can be used include mordenite, zeolite Y, zeolite L, zeolite $\Omega$, erionite, ferrierite, offretite, Silicalite, ZSM-5, etc. Additionally various two-dimensional layered materials can be used of the type $Zr(O_3PR)_2$, where R includes $-OH$, $-CH_2CH_2CO_2H$, and $-CH_2CH_2CH_2SO_3H$.

Encapsulation methods for noble metal crystallites comprise a series of steps, in particular sequence in order for the final catalyst to possess the distribution of crystallites residing entirely within the internal pore structure of the microcrystalline support. Three general methods are employed to incorporate the precursor complex within the support. The precursor complexes are selected from either various cationic metal amine species such as $Pt(NH_3)_4^{2+}$, $Rh(NH_3)_5Cl^{2+}$, $Ir(NH_3)_5Cl^{2+}$, $Pd(NH_3)_4^{2+}$, or $Ru(NH_3)_6^{3+}$ or suitable organometallic compounds including $Pt(allyl)_2$, $Pt(1,5-cyclooctadiene)_2$, $Pt(ethylene)_3$, $Rh(allyl)_3$, $Ir(allyl)_3$, or $Pd(allyl)_2$.

METHOD 1

A dilute (<0.1M) aqueous solution of the precursor compound exemplified by $Pt(NH_3)_4Cl_2$ is stirred with a slurry of the microcrystalline support (particle size typically less than 200 mesh) at room temperature or higher to effect an ion exchange between $Pt(NH_3)_4^{2+}$ and zeolite counterions such as $NH_4^+$ or $Na^+$ to the extent that $Pt(NH_3)_4^{2+}$ is incorporated within the support to ~0.1 to ~5.0 wt.% as Pt metal. Suitable supports for treatment by this ion-exchange method include the $NH_4^+$ or $Na^+$ forms of mordenite, zeolite Y, zeolite L, zeolite $\Omega$ (omega), and ZSM-5, although other monocations or mixtures of monocations in the zeolite may be used.

After an appropriate length of time, the $Pt(NH_3)_4^{2+}$/zeolite material is filtered and washed with water until no chloride counterion is detected in the filtrate. The solid catalyst precursor material is then dried in a vacuum oven at 50°–100° C. overnight then sieved to an appropriate particle size, typically below 200 mesh.

Preparation of the encapsulated catalyst from the $Pt(NH_3)_4^{2+}$/zeolite precursor material is accomplished in a flow reactor with the solid located between quartz wool plugs. The solid precursor may be diluted with inert particles of low-surface area alumina or silica of typically 8–14 mesh to lower the pressure drop across the bed and improve gas-solid contacting. After the solid is equilibrated in the reactor under an inert argon gas purge at 100° C., an atmosphere of $O_2/Ar$ is provided with a total flow rate of the gas blend of 400 ml/min. with 80 ml/min. of $O_2$ and 320 ml/min of Ar. The reactor furnace temperature is then increased at a rate of between 0.2°/min. and 10°/min. up to at least 350° C. and as high as 600° C. in certain instances. The $O_2$ flow is then stopped after reaching the desired temperature and Ar-purged for at least 3 hr. while cooling the reactor to 300° C. Then a flow of $H_2$ at 80 ml/min. is introduced into the Ar stream and maintained for 2–3 hr. The reactor is then cooled to 100° C. under an Ar purge of less than 320 ml/min. The above procedure serves to decompose the Pt-amine complex and results in the encapsulation of small Pt crystallites within the internal zeolite pore structure.

The Pt dispersion and particle sizes are evaluated by means of transmission electron microscopy (TEM). Ultramicrotomed thin (100 Å) sections of the Pt/zeolite particles embedded in an epoxy matrix provide the best means of examination. Metal particle sizes must be less than the diameter of the largest void space within the zeolite microstructure in order to be considered "encapsulated". Typically, the metal particles are no greater than 20 Å in size.

METHOD 2

Alternatively, the zeolites described in Method 1 must be used in the $NH_4^+$ form and calcined in a flow reactor in $O_2/Ar$ at 550° C. for 3 hr. or more. The anhydrous zeolite is then removed from the reactor and suspended in a predried hydrocarbon solvent such as hexane or toluene.

The metal is then introduced as a hydrocarbon-soluble complex [(e.g., $Pt(allyl)_2$, $Pt(1,5-cyclooctadiene)_2$, $Pt(ethylene)_3$, $Rh(allyl)_3$, $Ir(allyl)_3$, or $Pd(allyl)_2$] containing at least one ligand subject to elimination when contacted with the hydrocarbon slurry of the anhydrous zeolite. After stirring under a dry atmosphere for two or more days, the zeolite slurry is filtered then rinsed well with the hydrocarbon solvent. After drying at room temperature and under vacuum, the zeolite containing the adsorbed oxide-bound metal complex is treated under a $H_2$ or inert gas atmosphere in a flow reactor at 25°–200° C. for a length of time necessary to decompose the complex. The catalyst so prepared may be evaluated via TEM as described in Method 1.

METHOD 3

For acid stable zeolites with pore openings consisting of ten or fewer Si and/or Al and oxygen atoms (ten member rings or less) or pore openings less than 6.5 Å it is generally necessary to entrap the metal precursor complex directly in the internal zeolite pore structure during the zeolite synthesis. Synthetic zeolites of this type include erionite, ferrierite, offretite, and ZSM-5 or its all-silica analogue, Silicalite. Zeolite syntheses are performed as prescribed in U.S. Pat. Nos. 2,950,952 (Zeolite T or erionite), 3,966,883 (ferrierite), 4,093,699 (offretite), 3,702,886 (ZSM-5), and 4,067,724 (silicalite), except that ~0.5 to ~2.0 wt.-% as Pt of $Pt(NH_3)_4Cl_2$(or other noble metal amine complex) is added to the synthesis mixture.

The $Pt(NH_3)_4^{2+}$/zeolite catalyst precursor material obtained by this direct synthesis procedure is washed free of halide ions then optionally ion-exchanged at least three times with 2.2M $NH_4Cl$ solution. After all halide ions are again rinsed free of the material, it is dried in a vacuum oven at 50°–100° C. and sieved to an appropriate particle size, usually below 200 mesh. The encapsulated noble-metal zeolite composition is then obtained using the activation procedure described in Method 1.

For the encapsulated noble metal catalysts prepared using Method 1, it is desirable to perform the ion exchange of the metal complex cation on the $NH_4^+$ form of the zeolite in order for the final encapsulated catalyst to contain a high density of surface hydroxyl groups formed from decomposition of the $NH_4^+$ ions. The pore size and surface characteristics of those encapsulated metal/zeolite catalysts which may need further modification can be modified so as to discriminate between formaldehyde and various larger N-phosphonomethylamines such as $(HO)_2P(O)CH_2N(CH_2CO_2H)_2$ by the techniques outlined below.

(1) Solution Modification. Various soluble reagents "X" are reacted with a hydrocarbon (e.g., toluene) slurry of the anhydrous metal/zeolite catalyst using some or all of the steps listed below. A list of suitable "X" reagents includes chlorosilane monomers of the form $R_x^3R_y^4R_z^5SiCl_{4-x-y-z}$ ($0<x<3$, $0<y<2$, $0<z<1$, $R^3$ methyl, ethyl, propyl, isopropyl, butyl, phenyl, and $R^4$ and $R^5$ may also be selected from the list for $R^3$ in various combinations) and chloro-terminated polydimethylsiloxane oligomers of the form $ClSi(CH_3)_2O-(-Si(CH_3)_2-O-)_n-Si(CH_3)_2Cl$ (n=4, 5,6). The metal/zeolite catalyst is denoted as M/Z.

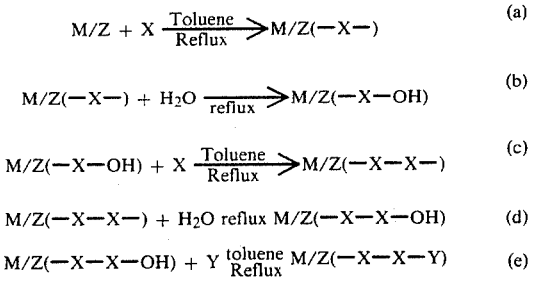

Steps (b) and (d) require vacuum dehydrations after their completion at 150°-200° C. and less than $10^{-3}$ torr. Reagent Y is selected from various volatile trimethylsilyl-transfer agents such as $(CH_3)_3SiCl$ or $(CH_3)_3SiNHSi(CH_3)_3$.

(2) Vapor-Phase Modification. The encapsulated metal/zeolite catalysts may also be modified by gas-phase reagents at temperatures above the boiling point of the reagent to 600° C. in a flow reactor. Reagents envisioned for use by this method include $(CH_3)_3SiCl$, $(CH_3)_3SiNHSi(CH_3)_3$, $Si(OR^6)_4$ ($R^6$=methyl, ethyl), and $Ti(OR^7)_4$ ($R^7$=isopropyl, butyl).

(3) Catalyst Precursor Modification. Catalyst precursors prepared by means of Method 1 above may be impregnated after drying with various Si- or Ti-containing compounds including $Si(OR^6)_4$, $Ti(OR^7)_4$, and

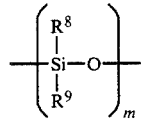

where this silicone is of the type described in U.S. Pat. No. 4,402,867 and $R^8$ and $R^9$ are individually selected from the group consisting of hydrogen, methyl, fluorine, chlorine, and hydroxy, and m is an integer of at least 3. The impregnated catalyst precursor (e.g., $Pt(NH_3)_4^{2+}$/zeolite) is then dried in a vacuum, sieved to the appropriate particle size, and charged to a flow reactor. Treatment in $O_2$/Ar followed by $H_2$/Ar is identical to the procedure given in Method 1.

Oxidation procedures were conducted in a 300-ml 316 stainless steel "Magnedrive" autoclave from Autoclave Engineers. A continuous flow through the reactor of $O_2$ at 150-60 cc/min was used to purge the reactor of the $CO_2$ by-product. The extent of the oxidation was continuously monitored by the cumulative total of $CO_2$ in the $O_2$ off gas and detected using a Wilks Miran II Process Analyzer. Typically, a 2.0 ml charge of 37% formaldehyde solution was added to 98.0 ml of water and the mixture charged along with 0.10 to 0.25 g of catalyst. The N-phosphonomethylamine was added as a solid by means of injection with $O_2$ pressure into the reactor at the appropriate time without disassembling the autoclave. Formaldehyde could also be added in this fashion. Formaldehyde oxidations in the absence and the presence of the N-phosphonomethylamine were performed at 95±3° C., 30 psig $O_2$(206.85 kPa at the flow rate given above, and 1500 rpm stirring rate.

EXAMPLE 1

A platinum-encapsulated catalyst was prepared by ion exchange of an aqueous slurry of Union Carbide LZM8, $NH_4$-mordenite ($NH_4$—MOR) in a 0.023M solution of $Pt(NH_3)_4Cl_2$. After stirring overnight the slurry was filtered then rinsed by resuspension in water followed by filtration until chloride ion was no longer detected in the filtrate. The $Pt(NH_3)_4^{2+}/NH_4$—MOR catalyst precursor was vacuum dried overnight at 80° C. then sieved to below 200 mesh. A mixture of 1.5 g of $Pt(NH_3)_4^{2+}/NH_4$—MOR and 7.0 cc of $8\times14$ mesh $Al_2O_3$ was charged to a quartz reactor tube and contained with quartz wool plugs. The reactor was equilibrated at 100° C. under $\sim$10 cc/min Ar purge. With a flow of 80 cc/min $O_2$ and 320 cc/min. Ar, the reactor was increased in temperature at 0.2°/min. to 350° C. The $O_2$ flow was then discontinued as the reactor was cooled to 300° C. After 3 hr. a flow of 80 cc/min. $H_2$ was introduced into the 320 cc/min. gas stream for a 2 hr. period. The reactor was then cooled to 100° C. The 3.30% Pt/H—MOR catalyst so treated was recovered and found to have no Pt crystallites in excess of 20 Å as seen from transmission electron microscopy.

The catalyst was evaluated in the 300-ml autoclave for formaldehyde oxidation as previously described and as summarized in Table 1. By comparison, a catalyst that is not encapsulated shows little formaldehyde oxidation activity once contacted with N-phosphonomethylglycine (see Table II). Additionally, as can be seen in the reaction data displayed between formaldehyde charges 10 and 14 in Table I these encapsulated catalysts differ from conventional supported noble metal catalysts (Pt/C) in that they can be washed free of adsorbed poisons (glyphosate) and this simple regenerative procedure restores the initial activity (charges 2 and 3 in Table I).

Mesh sizes given in Example 1 or elsewhere in the specification are those of the U.S. Standard Sieve Series.

TABLE I

Autoclave Evaluation Data for 3.30% Pt/H—MOR[a] for Formaldehyde Oxidation in the Absence and Presence of N—Phosphonomethylglycine

| Formaldehyde Charge No. | Reaction Time, Min. | Formaldehyde Conversion, % |
|---|---|---|
| 1 | 51 | 87.3 |

TABLE I-continued

Autoclave Evaluation Data for 3.30% Pt/H—MOR[a] for Formaldehyde Oxidation in the Absence and Presence of N—Phosphonomethylglycine

| Formaldehyde Charge No. | Reaction Time, Min. | Formaldehyde Conversion, % |
|---|---|---|
| 2[b] | 24 | 100.0 |
| 3[c] | 21 | 100.0 |
| 4 | 54 | 100.0 |
| 5 | 45 | 100.0 |
| 6 | 54 | 100.0 |
| 7[d] | 36 | 100.0 |
| 8 | 39 | 100.0 |
| 9[e] | 117 | 96.9 |
| 10 | 48 | 45.9 |
| 11[f] | 30 | 100.0 |
| 12 | 27 | 100.0 |
| 13 | 27 | 100.0 |
| 14[c] | 45 | 100.0 |
| 15 | 60 | 96.5 |
| 16 | 27 | 2.55 |
| 17[f] | 78 | 100.0 |
| 18 | 45 | 100.0 |
| 19 | 45 | 100.0 |
| 20[c] | 117 | 90.3 |
| 21 | 33 | 8.49 |

[a]Initial autoclave charge: 0.10 g. Platinum loading determined by elemental analysis.
[b]Total catalyst charge is now 0.25 g.
[c]Added 0.20 g of N—phosphonomethylglycine
[d]Added another 0.20 g of N—phosphonomethylglycine; total charge: 0.40 g.
[e]Residual catalyst activity after stirring ~65 hr. in a solution of 0.40 g of N—phosphonomethylglycine.
[f]Catalyst filtered off, rinsed with water, and returned to the autoclave.

TABLE II

Autoclave Evaluation Data for ~2% Pt/CPG[a] for Formaldehyde Oxidation in the Absence and Presence of N—Phosphonomethylglycine

| Formaldehyde Charge Number | Reaction Time, Min. | Formaldehyde Conversion, % |
|---|---|---|
| 1 | 21 | 100.0 |
| 2 | 21 | 100.0 |
| 3 | 21 | 100.0 |
| 4[b] | 37 | 9.3 |

[a]Catalyst prepared with 100% controlled pore glass (CPG) of 200-400 mesh by incipient wetness method with aqueous Pt(NH$_3$)$_2$(NO$_2$)$_2$. Catalyst charge: 0.25 g.
[b]Added 0.30 g of N—phosphonomethylglycine.

EXAMPLE 2

Some platinum-encapsulated catalysts require further functionalization in order to tailor the pore size and surface adsorption sites selectively to entry of formaldehyde into the internal pore structure in the presence of N-phosphonomethylglycine in the bulk solution. To illustrate this point a sample of Union Carbide NaY(L-ZY72) was thoroughly exchanged three times with 2.2M NH$_4$Cl solution. The NH$_4$Y zeolite was then exchanged with a 0.015M solution of Pt(NH$_3$)$_4$Cl$_2$. The Pt(NH$_3$)$_4{}^{2+}$/NH$_4$Y precursor catalyst was dried in a vacuum oven at 80° C. overnight then sieved to below 200 mesh. The precursor catalyst was then charged to a quartz flow reactor between quartz wool plugs, purged with Ar at 100° C., and treated with O$_2$/Ar while the furnace temperature was ramped to 600° C. The thermal ramping rate was 2°/min. to 250° C. then 0.5°/min. up to 600° C. After 3-hr. purge in Ar while the reactor cooled to 300° C., an H$_2$/Ar gas mixture was passed through the catalyst bed for 2 hr. The reactor was cooled to 100° C. in an Ar gas purge.

The catalyst prepared by the above method showed significant poisoning within the time that two charges of formaldehyde were added in sequence. The results are shown in Table III.

TABLE III

Autoclave Evaluation Data for ~3% Pt/HY[a] for Formaldehyde Oxidation in Absence and Presence of N—Phosphonomethylglycine

| Formaldehyde Charge Number | Reaction Time, Min. | Formaldehyde Conversion, % |
|---|---|---|
| 1 | 18 | 100.0 |
| 2 | 18 | 100.0 |
| 3 | 18 | 100.0 |
| 4[b] | 42 | 100.0 |
| 5 | 42 | 47.5 |

[a]Catalyst charge: 0.10 g.
[b]Added 0.20 g of N—phosphonomethylglycine.

In contrast, surface modification of the ~3% Pt/HY using chlorine-terminated polydimethylsiloxane (Cl—PDMSi—Cl, Petrarch Systems PS375) extended the number of formaldehyde oxidation cycles completed once N-phosphonomethylglycine was added. The Pt/HY catalyst was prepared using an identical procedure to the catalyst in Table III. However, after oxidation in O$_2$/Ar followed by reduction in H$_2$/Ar, the catalyst was recovered in an N$_2$-containing drybox. The catalyst powder was then treated with an excess of Cl-PMDSi-Cl, diluted with dry toluene, and refluxed overnight as a suspension in toluene. The treated catalyst designated ~3% Pt/HY(—PDMSi—) was filtered in air, washed with hexanes, and dried in a vacuum oven at 115° C. overnight. A sample of this catalyst gave the results shown in Table IV.

TABLE IV

Autoclave Evaluation Data for ~3% Pt/HY(—PDMSi—)[a] for Formaldehyde Oxidation in the Absence and Presence of N—Phosphonomethylglycine

| Formaldehyde Charge Number | Reaction Time, Min. | Formaldehyde Conversion, % |
|---|---|---|
| 1 | 21 | 100.0 |
| 2[b] | 18 | 100.0 |
| 3 | 21 | 100.0 |
| 4 | 21 | 100.0 |
| 5[c] | 21 | 100.0 |
| 6 | 21 | 100.0 |
| 7[b] | 48 | 100.0 |
| 8 | 54 | 63.7 |

[a]Catalyst charge: 0.15 g.
[b]Added 0.20 g of N—phosphonomethylglycine.
[c]Catalyst filtered off, rinsed with water, and returned to autoclave.
The surface modified catalyst shown in Table IV extends the poisoning resistance by 2-3 cycles over the catalyst in Table III.

A co-catalyst as described herein can be usefully employed in processes to convert N-phosphonomethyliminodiacetic acid to N-phosphonomethylglycine under conditions in general effective for such conversion, including those taught in the referred-to U.S. Pat. No. 3,969,398. Thus the conversion can be carried out under conditions described in the following example.

EXAMPLE 3

To a 300 ml. autoclave as described above 100 ml. deionized water, 1 gram of Norit A activated carbon, and 4 grams N-phosphonomethyliminodiacetic acid are charged. There is also added a 0.15 gram amount of the 3.30% Pt/H—MOR catalyst of Example 1. The contents are heated to 90° C. with oxygen flowing at atmospheric pressure. The contents are heated to about 95° C. with agitation for approximately two hours, with yields of N-phosphonomethylglycine in excess of 95% expected to be obtainable. Because of the effectiveness of the noble metal catalyst in oxidizing the formaldehyde, the moles of CO$_2$ generated may be expected to approach 1.9 or so for each mole of reactant, with the amount of formaldehyde remaining being less than 10% of theoretical and in concentrations possibly around 0.1% or lower by weight. Thus the tendency of formaldehyde to react with the N-phosphonomethylglycine product will be markedly diminished.

While the present encapsulated catalysts are of particular interest for oxidation of formaldehyde in the presence of N-phosphonomethylglycine or other products of oxidative cleavage reactions of N-phosphonomethylaminodiacetic acid or other glycine derivatives, the catalysts will also be useful for oxidation in the presence of other catalyst poisons having size and zeolite diffusion characteristics like those of N-phosphonomethylglycine. Various amines and other nitrogen bases are capable of poisoning the noble metal oxidation catalysts, and encapsulation in porous carriers as taught herein is effective in avoiding or inhibiting such poisoning in a number of cases, particularly when the poison is a relatively large molecule, such as of molecular weight over 100, or even over 150. Even if poisoning is not avoided, the encapsulated catalyst may still show some improvement in activity and life over a catalyst in which the active metal has not been protected. The value of various degrees of improvement may depend upon the particular application. However, it is apparent that an encapsulated catalyst can be considered effectively protected against a particular poison in a formaldehyde oxidation, if it makes possible nearly quantitative oxidation of formaldehyde under practical conditions in the presence of such poison, in a reasonable time period, such as half-an-hour to an hour or so. Ethylenediaminetetracetic acid, quinaline and 4-methylquinoline are examples of nitrogen bases against which encapsulated catalysts can provide protection in accord with the present invention.

A number of catalysts were prepared in accord with procedures described herein, and their characterization by transmission electron microscopy is reported in Table V, along with that of a platinum on silica catalyst. The catalyst description includes the percentage of platinum in the catalyst.

TABLE V

Summary of Platinum Catalysts and Their Characterization by Transmission Electron Microscopy

| Catalyst Description | Catalyst Support Particle Size[a] ($\mu$m) | TEM Data[b] Pt Particle Sizes Å | Distribution[c] |
|---|---|---|---|
| 1.79% Pt/SiO$_2$ | 74–595[d] | 15–40 | M |
| 2.90% Pt/HY | 1.47 | 10–20 | M |
| 3.23% Pt/HY(—PDMSi—)[e] | 1.48 | 10–15 | M |
| 3.30% Pt/H—MOR | 1.06 | 9–18 | M |
| 3.57% Pt/H—MOR | 1.06 | 9–18 | M |
| 2.62% Pt/H—ZSM-5 | 5.90 | 10–15 | M |
| 3.54% Pt/H—ZSM-5 | 5.54 | 10–20 | C |
| 0.38% Pt/H—ZSM-5 | 5.54 | 13–40 | C |
| 3.1% Pt/H—ZSM-5 | —[f] | 15–44 75–200 | C |

[a]Particle size determined from Coulter Counter measurements and reported as the average value unless otherwise noted.
[b]Specimens were in most cases (100 keV) ultramicrotomed sections of the catalyst embedded in epoxy resin.
[c]Codes for the observed metal dispersions: M = monomodal, C = continuous range of particle sizes.
[d]Particle size range for microspheroidal silica, Grace Grade 56.
[e]PDMSi = polydimethylsiloxane oligomer attached to the zeolite surface by the reaction between the reduced Pt/HY sample (surface silica hydroxyl groups) and chlorine-terminated PDMSi in dry toluene.
[f]Particle size not determined.

The effect of various nitrogen bases on formaldehyde oxidation with various platinum catalyst was determined and reported in Table VI below. All experiments were conducted in a 300-mL Autoclave Engineers Magnedrive autoclave run at 1500 rpm at a temperature of 95° C. and 30 psig O$_2$. A continuous flow of O$_2$ (mixed with CO$_2$ product) at 150–60 cm/min. afforded a means to monitor the conversion of the formaldehyde substrate with a calibrated Wilks Miran II Process Analyzer (IR detector). Typically 2.0 mL of 37% formaldehyde solution, 100-mL of water, and 0.10 to 0.50 g of catalyst was charged to the autoclave. Except where noted, 3.4×10$^{-4}$ moles of nitrogen base were charged to the reactor. All Pt/zeolite samples used were in the "Pt-encapsulated" form. H$_4$EDTA=Ethylenediaminetetraacetic acid.

TABLE VI

Summary of the Effect of Various Nitrogen Bases on the Formaldehyde Oxidation Endpoint with Various Platinum Catalysts

| Catalyst | No Base 100% Conversion (min.) | Endpoint (min.) with Nitrogen Base (% Conversion) | | | | |
|---|---|---|---|---|---|---|
| | | Glycine | H$_4$EDTA | Pyridine | Quinoline | 4-methyl-quinoline |
| 1.79% Pt/SiO$_2$ | 45 | 60(5.2) | 60(57.5) | 39(6.7) | 60(16.7) | — |
| 2.93% Pt/HY | 18 | 60(15.4) | 60(52.8) | — | — | — |
| 3.23% Pt/HY(—PDMSi—) | 16 | 60(17.9) | 15(100) 18(100)[a] 27(99.6) 60(64.4) | — | — | — |
| 3.5% Pt/H—MOR | 20 | 60(55.5) | 21(100) 21(100) 21(100) | 60(89.2) 60(74.2) | 24(100) 24(100) 24(100) 21(100) | — |
| 3.54% Pt/H—ZSM-5 | 20 | 60(75.1) | 27(100) | 60(20.3) | 60(40.9) | 18(100) |

TABLE VI-continued

Summary of the Effect of Various Nitrogen Bases on the Formaldehyde Oxidation Endpoint with Various Platinum Catalysts

| Catalyst | No Base 100% Conversion (min.) | Endpoint (min.) with Nitrogen Base (% Conversion) | | | | |
|---|---|---|---|---|---|---|
| | | Glycine | H$_4$EDTA | Pyridine | Quinoline | 4-methyl-quinoline |
| | | 60(78.8) | 33(100) | | | 18(100) |
| | | | 36(99.5) | | | 18(100) |
| | | | | | | 18(100) |
| 3.17% Pt/H—ZSM-5 | 18 | — | — | — | — | 24(100) |
| | | | | | | 24(100) |
| | | | | | | 24(100)$^b$ |
| | | | | | | 27(100) |
| | | | | | | 27(100)$^c$ |
| | | | | | | 45(100) |
| | | | | | | 45(100) |
| | | | | | | 54(100)$^d$ |
| | | | | | | 54(100) |

$^a$Here and in succeeding experiments, these data represent subsequent formaldehyde cycles with a fresh formaldehyde charge.
$^b$4-Methylquinoline total charge: 6.8 × 10$^{-4}$ moles.
$^c$4-Methylquinoline total charge: 3.4 × 10$^{-3}$ moles.
$^d$Formaldehyde oxidation endpoint after 24 hrs. in 0.034 M 4-methylquinoline.

I claim:

1. The method of oxidizing formaldehyde or formic acid in the presence of an N-phosphonomethyl amine which comprises contacting a liquid solution containing formaldehyde or formic acid and an N-phosphonomethylamine with oxygen in the presence of a catalyst comprising a microporous support with a noble metal oxidation catalyst located within the pores of such support, with the support being a microporous acid resistant aluminosilicate having an Si to Al ratio of at least 2 and with the microporous support being selectively permeable so as to inhibit contact of the N-phosphonomethylamine with the noble metal therein, at a temperature sufficiently elevated to effect the desired oxidation.

2. The method of claim 1 in which the formaldehyde or formic acid are produced as by-products in an oxidative cleavage reaction of an N-phosphonomethylamine to produce a different N-phosphonomethylamine compound, with such reaction involving use of an active carbon catalyst.

3. The process of claim 1 in which the aluminosilicate is a zeolite of the mordenite class.

4. The process of claim 1 in which the catalyst is a zeolite containing platinum crystallites within the pores and generally of diameters no greater than 20 Å as measured by transmission electron microscopy.

5. The method of claim 1 in which the noble metal catalyst is used as a co-catalyst along with activated carbon catalyst to effect oxidative cleavage of N-phosphonomethyliminodiacetic acid to N-phosphonomethylglycine and concurrent oxidation of the formaldehyde by-product.

6. The method of claim 5 in which the oxidation is conducted at temperatures of 25° to 200° C. and oxygen pressures of 50 to 20,000 kPa.

7. The method of claim 5 in which the oxidation is conducted at temperatures of 75° to 150° C. and pressures of 100 to 700 kPa.

8. The method of claim 1 in which the catalyst has been modified by a chlorosilane compound, a chloro-terminated siloxane oligomer, or a silicone polymer.

9. The method of claim 1 in which the microporous support is a zeolite characterized by pore openings no greater than about 8 Å.

10. The method of claim 1 in which the microporous support is characterized by pore openings no greater than about 5 Å and platinum has been incorporated in the zeolite during its preparation.

11. The method of oxidizing formaldehyde of formic acid with a noble metal catalyst in a waste stream which comprises contacting a waste stream containing formaldehyde or formic acid with oxygen in the presence of a catalyst comprising a microporous support with a noble metal catalyst located within the pores of such support, with the support being a microporous, acid resistant aluminosilicate having an Si to Al ratio of at least 2, and with the waste stream also containing a poison for the noble metal and the microporous support being selectively permeable so as to inhibit contact of the poison with the metal therein.

* * * * *